(12) United States Patent
Almulhim

(10) Patent No.: US 12,108,948 B1
(45) Date of Patent: Oct. 8, 2024

(54) SURGICAL DEEP CURVED RETRACTOR WITH LED LIGHT FOR LAPAROTOMY

(71) Applicant: KING FAISAL UNIVERSITY, Al-Ahsa (SA)

(72) Inventor: Abdulrahman Saleh Almulhim, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/482,615

(22) Filed: Oct. 6, 2023

(51) Int. Cl.
*A61B 17/02* (2006.01)
*A61B 90/30* (2016.01)

(52) U.S. Cl.
CPC .......... *A61B 17/0281* (2013.01); *A61B 90/30* (2016.02); *A61B 2090/309* (2016.02)

(58) Field of Classification Search
CPC . A61B 17/02; A61B 17/0206; A61B 17/0281; A61B 90/30; A61B 90/309
USPC ........................................................ 600/212
See application file for complete search history.

(56) References Cited

U.S. PATENT DOCUMENTS

| | | | |
|---|---|---|---|
| 5,201,325 A | 4/1993 | McEwen et al. | |
| 6,210,325 B1 | 4/2001 | Bartie et al. | |
| 2007/0060795 A1 | 3/2007 | Vayser et al. | |
| 2013/0237768 A1* | 9/2013 | Heftman | A61B 17/0218 600/228 |
| 2018/0228483 A1 | 8/2018 | Duggal et al. | |
| 2019/0105026 A1* | 4/2019 | Arshava | A61B 17/02 |
| 2020/0046336 A1 | 2/2020 | Swift et al. | |
| 2021/0145426 A1* | 5/2021 | Swift | A61B 17/02 |

* cited by examiner

*Primary Examiner* — Eduardo C Robert
*Assistant Examiner* — Christina NegrelliRodriguez
(74) *Attorney, Agent, or Firm* — Nath, Goldberg & Meyer; Joshua B. Goldberg

(57) ABSTRACT

The surgical retractor includes an elongated shaft, a handle at a proximal end of the elongated shaft; and an illuminating LED light, wherein the elongated shaft is capable of having up to four bends, with the illuminating LED light located on the elongated shaft adjacent to one of the up to four bends. The elongated shaft may be formed from an elastically deformable material. The elongated shaft can have four bends configured such that the distal end of the elongated shaft is parallel to the proximal end of the elongated shaft. The surgical retractor may be configured for use in a laparotomy.

7 Claims, 1 Drawing Sheet

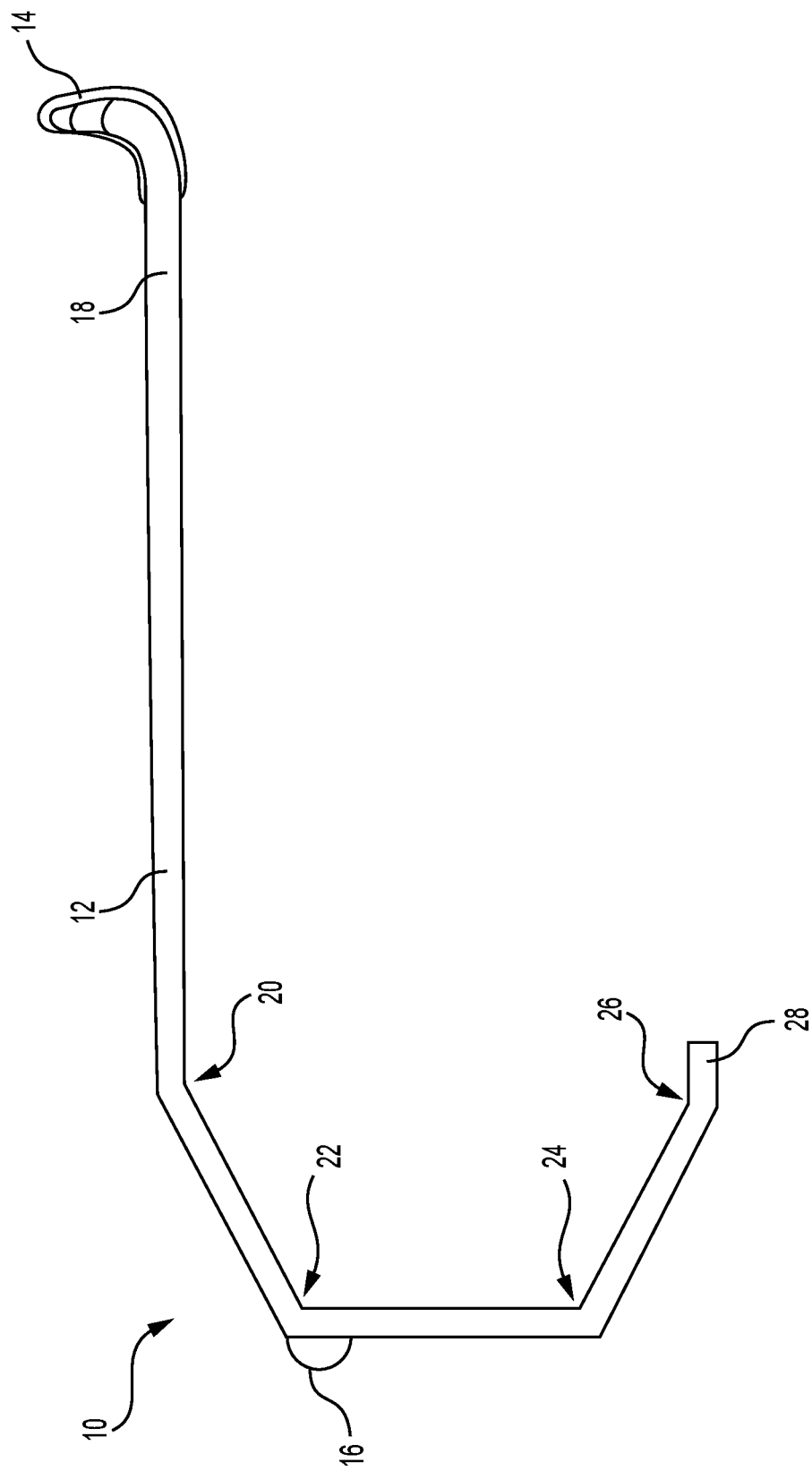

SURGICAL DEEP CURVED RETRACTOR WITH LED LIGHT FOR LAPAROTOMY

BACKGROUND

1. Field

The disclosure of the present patent application relates to surgical instruments, and particularly to a surgical deep curved retractor for laparotomies.

2. Description of the Related Art

While performing a surgical procedure, a surgeon may utilize a retractor, which may allow the surgeon to draw lateral and deep layers of tissue away from underlying features and/or structures. Responsive to the drawing or retracting of lateral and deep layers away from underlying features, a surgeon may focus his or her attention on repair, manipulation, and/or replacement of body organs, and/or other anatomical structures including, but not limited to, soft tissue, nerve, venous, arterial, tendinous, and bony structures, and/or may perform numerous other surgical procedures.

However, at times, a surgical instrument and/or other operating room equipment may give rise to shadowing of light from an overhead source intended to illuminate a surgical area of interest. Other sources of blockage or limiting of overhead light may include the surgeon's head, body, and/or hands, for example, and/or one or more body parts of an assistant. Further, other instrumentation in and around the surgical field may obscure the surgical field from the surgeon's view. Accordingly, a surgeon may be required to reposition surgical instruments and/or overhead lighting or may be required to wear a headlamp so as to provide a clear and/or illuminated view of a surgical area of interest.

One approach toward achieving better control over illumination of a surgical area of interest may include use of fiber-optic conduits in a surgical retractor so as to provide local illumination of, for example, a surgical field (or portion thereof). However, fiber-optics-based illuminated surgical retractors may be attached to cables, such as electrical and/or fiber-optic cables, which may impede a surgeon's freedom to orient a surgical retractor into a desired position. Additionally, fiber-optics-based retractors may direct illumination predominately along the longer dimension of a surgical retractor, without providing sufficient illumination directly beneath the retractor. Further, fiber-optics-based retractors may comprise rigid structures that may be unable to conform to a curvature dictated by a structure or feature within a surgical area of interest so as to permit illumination within, for example, small openings of a human or animal body.

Thus, a surgical retractor solving the aforementioned problems is desired.

SUMMARY

In an embodiment, the surgical retractor includes an elongated shaft, a handle at a proximal end of the elongated shaft; and an illuminating LED light, wherein the elongated shaft is capable of having up to four bends, with the illuminating LED light located on the elongated shaft adjacent to one of the up to four bends. As a non-limiting example, the elongated shaft may be formed from an elastically deformable material. As another non-limiting example, the elongated shaft can have four bends configured such that the distal end of the elongated shaft is parallel to the proximal end of the elongated shaft. As a further non-limiting example, the surgical retractor may be configured for use in a laparotomy.

These and other features of the present subject matter will become readily apparent upon further review of the following specification.

BRIEF DESCRIPTION OF THE DRAWINGS

The sole drawing FIGURE shows a side view of a surgical retractor.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats, and the like.

"Patient" as used herein refers to a subject in need of treatment of a condition, disorder, or disease.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to a surgical retractor 10 including an elongated shaft 12, a handle 14 at a proximal end 18 of the elongated shaft 12, and an illuminating light-emitting diode (LED) light 16, wherein the elongated shaft 12 is capable of having up to four bends. As shown in the sole drawing FIGURE, the elongated shaft 12 can have four bends 20, 22, 24, 26, with the illuminating LED light 16 located on the elongated shaft 12 adjacent to one of the four bends 20, 22, 24, 26, in this non-limiting example, adjacent to bend 22.

Each of the four bends 20, 22, 24, 26 of the elongated shaft 12 can be bent at an angle of about 30 to about 45 degrees. Accordingly, the four bends 20, 22, 24, 26 of the elongated shaft 12 can be configured such that a distal end 28 of the elongated shaft 12 is parallel to the proximal end 18 of the elongated shaft 12. In this regard, a fourth bend 26 of the four bends 20, 22, 24, 26 can be located close to the distal end 28 of the elongated shaft 12.

The surgical retractor 10 may be configured for use in conducting a laparotomy. In a non-limiting example, the laparotomy can be conducted in a patient's abdominal cavity.

It should be understood that the surgical retractor 10 may be formed from any suitable material(s). As a non-limiting example, the elongated shaft 12 may be formed from an elastically deformable material. Alternatively, the elongated shaft 12 may be formed from a solid material including, by way of non-limiting example, steel, steel alloy, aluminum, titanium, plastic, ceramic, fluidized metal, or any combination thereof.

It should be understood that additional components known to be used with surgical instruments may also be used with the surgical retractor 10.

It is to be understood that the surgical retractor described herein is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A surgical retractor, comprising:
an elongated shaft;
a handle at a proximal end of the elongated shaft; and
an illuminating LED light,
wherein the elongated shaft has four bends, with the illuminating LED light located on the elongated shaft adjacent to a second bend of the four bends,
wherein each of the four bends is bent at an angle of about 30 to about 45 degrees, and
wherein a distance from a distal end of the elongated shaft to a fourth bend of the four bends of the elongated shaft is shorter than a distance from a first bend of the four bends of the elongated shaft to the proximal end of the elongated shaft.

2. The surgical retractor of claim 1, wherein the fourth bend of the four bends is located close to the distal end of the elongated shaft.

3. The surgical retractor of claim 1, wherein the four bends are configured such that the distal end of the elongated shaft is parallel to the proximal end of the elongated shaft.

4. The surgical retractor of claim 1, configured for conducting a laparotomy.

5. The surgical retractor of claim 4, wherein the laparotomy is conducted in a patient's abdominal cavity.

6. The surgical retractor of claim 1, wherein the elongated shaft comprises an elastically deformable material.

7. The surgical retractor of claim 1, wherein the elongated shaft comprises steel, steel alloy, aluminum, titanium, plastic, ceramic, fluidized metal, or any combination thereof.

* * * * *